United States Patent [19]
Gelfand

[11] 4,092,369
[45] May 30, 1978

[54] PROCESS FOR THE PREPARATION OF CHLOROALKYLBENZENE CHLORIDES

[75] Inventor: Samuel Gelfand, Lewiston, N.Y.

[73] Assignee: Hooker Chemicals & Plastics Corp., Niagara Falls, N.Y.

[21] Appl. No.: 704,729

[22] Filed: Jul. 12, 1976

Related U.S. Application Data

[63] Continuation of Ser. No. 547,079, Feb. 4, 1975, abandoned.

[51] Int. Cl.$^2$ ............................................ C07C 17/14
[52] U.S. Cl. .............................................. 260/651 R
[58] Field of Search .................................. 260/651 R

[56] References Cited

U.S. PATENT DOCUMENTS

| | | | |
|---|---|---|---|
| 1,345,373 | 7/1920 | Kyrides | 260/651 R |
| 2,695,873 | 11/1954 | Loverde | 260/651 R |
| 2,926,201 | 2/1960 | Dreisbach et al. | 260/651 R |

OTHER PUBLICATIONS

Boesken et al., Chem. Abstracts, 5, 3399 (1911).

Groggins, Unit Processes in Organic Synthesis, 5th Edition, pp. 234-235 (1958).

*Primary Examiner*—C. Davis
*Attorney, Agent, or Firm*—Peter F. Casella; William J. Crossetta, Jr.; Arthur S. Cookfair

[57] ABSTRACT

A process for the selective monoα-chlorination of alkyl chloroaromatic compounds comprises reacting chlorine with an alkyl chloroaromatic compound of the formula:

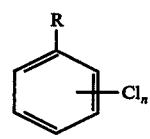

where R is methyl or ethyl and $n$ is 1 or 2; in the presence of an organic sulfide catalyst selected from the group consisting of aryl sulfides, alkyl sulfides, alkylaryl sulfides and heterocyclic sulfides.

23 Claims, No Drawings

PROCESS FOR THE PREPARATION OF CHLOROALKYLBENZENE CHLORIDES

This is a continuation, of application Ser. No. 547,079, filed Feb. 4, 1975, now abandoned.

BACKGROUND OF THE INVENTION

It is known that alkyl chloroaromatic compounds having one or more hydrogen atoms attached to the α-carbon atoms of the side chain are reactive when treated with chlorine in the presence of ultraviolet radiation. Under such conditions, substitution of one or more of these hydrogen atoms, often referred to as benzylic, or α-hydrogen atoms, by chlorine, normally occurs. It is also known that it is difficult to limit replacement to only one of these hydrogen atoms with chlorine under these conditions, since a second and often a third hydrogen atom may also be replaced, giving rise to the formation of a mixture of mono and poly-α-chlorinated alkyl aromatic compounds. From a commercial point of view such prior art processes have serious drawbacks where the objective is the preparation of the commercially desirable monoα-chlorinated compound. The mono α-chlorinated products are of commercial importance as intermediates in the production of pesticides and in the preparation of quarternary ammonium compounds for use as disinfectants and the like. The formation of mixtures of mono and polychlorinated compounds requires additional separation steps to isolate the desired α-chlorinated compound, thus adding to the complexity and cost of the process.

One solution to this problem in the prior art processes has been to minimize the formation of poly α-chlorinated compounds by greatly limiting the degree of completion to which the chlorination reaction is carried. However, although this practice minimizes the formation of poly α-chlorinated compounds, it has the disadvantage of requiring a large amount of recycle thus making the process inefficient and more expensive.

Accordingly, it is a primary object of this invention to provide an improved process for the selective mono α-chlorination of alkyl chloroaromatic compounds. It is a further object to provide such a process whereby the formation of polychlorinated compounds is minimized, allowing the chlorination reaction to be carried more nearly to completion than is feasible in the prior art processes. It is a still further object to provide a catalytic process for the selective mono α-chlorination of alkyl chloroaromatic compounds that may be carried out in the absence of ultraviolet radiation. Additional objects and advantages of the present invention will become apparent to those skilled in the art from the following description.

SUMMARY OF THE INVENTION

The present invention provides a process for the selective mono α-chlorination of substituted alkyl aromatic compounds which comprises reacting chlorine with an alkyl chloroaromatic compound of the formula:

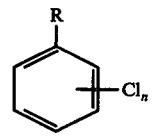

wherein R is methyl or ethyl and $n$ is 1 or 2; in the presence of an organic sulfide catalyst.

the alkyl chloroaromatic compounds which may be α-chlorinated in accordance with this invention include those of the formula set forth hereinabove, where the chlorine(s) may be present in the ortho, meta, or para positions. The preferred compounds are monochlorotoluene and, in particular, parachlorotoluene and orthochlorotoluene.

Organic sulfides which may be employed as catalysts in the process of this invention are characterized by the presence of divalent sulfur and include, for example, aryl sulfides, alkyl sulfides, alkylaryl sulfides, heterocyclic sulfides and the like as well as mixtures thereof. Typical examples of such organic sulfides characterized by the presence of divalent sulfur are dipropyl sulfide, dibutyl sulfide, dioctyl sulfide, diphenyl sulfide, bis(p-chlorophenyl) sulfide, thiophene, tetrachlorothiophene and the like as well as mixtures these sulfides.

It has been found that catalysts of the type disclosed hereinabove, when employed in the process of the present invention, direct the chlorination reaction in a highly specific manner to effect the mono α-chlorination of the alkyl aromatic compound, thus permitting the reaction to be carried out much closer to stoichiometric completion, without formation of substantial amounts of poly α-chlorinated products, than is possible utilizing the photo-catalyzed process of the prior art.

The effectiveness of organic sulfides to direct a highly specific side chain chlorination is especially surprising in view of the known use of such compounds as para-directing co-catalysts for the nuclear chlorination of aromatic compounds. It is known, for example, from U. S. Patent 3,226,447, that organic sulfides may be employed as co-catalysts with an iron, aluminum, or antimony halide catalyst in the nuclear chlorination of benzene, chlorobenzene or toluene. In contrast, when such catalysts are employed in the process of this invention in the chlorination of alkyl chloroaromatic compounds, little or no nuclear chlorination occurs.

Although many variations of the process of this invention are possible and will be apparent to those skilled in the art, the process is typically carried out in the following manner:

The alkyl chloroaromatic compound to be α-chlorinated is charged to a reaction vessel together with a catalytic amount of the organic sulfide. Preferably, agitation of the reaction mixture is provided. Although reaction temperature is not critical, it is preferred to effect the reaction at a temperatur in the range of about 20° to about 80° Celsius, and most preferably in the range of 35° to 70° Celsius. Chlorine gas is introduced into the reaction mixture until the reaction has been carried out to the desired degree of completion. Preferably the reaction is continued until about 30 to about 95 percent, and most preferably about 60 to 90% of the stoichiometric amount of chlorine has been added. Although the process of this invention is preferably carried out at atmospheric pressure, sub-atmospheric or super-atmospheric pressures may be employed, if desired. Upon completion of the reaction, the reaction mixture may be purged with nitrogen, air, or other gas to remove hydrogen chloride and any residual chlorine. The desired mono α-chlorinated product may then be separated from the reaction mixture by known means such as distillation.

The amount of catalyst employed is not critical, but is typically in a range of about 0.1 to about 10.0 percent by weight, based on the weight of alkyl chloroaromatic starting material. Preferably, the amount of catalyst is in the range of about 0.5 to about 1.0 percent by weight based on the weight of alkyl chloroaromatic starting material.

The presence of incident light is not required to allow α-chlorination to take place in accordance with the present process. Thus, when an alkyl chloroaromatic compound, such as parachlorotoluene is chlorinated in accordance with this invention, closely comparable results are obtained in the presence or absence of incident light.

The examples set forth herein below will serve to further illustrate the invention and the manner in which it may be practiced. From the data presented, the advantages of the process of this invention over photochemical chlorination processes will be apparent. The present process will be seen to afford higher yields of α-monochlorinated product and lesser amounts of α-, α-dichlorinated or higher chlorinated materials at comparable or greater conversion levels than are attainable from photochemical chlorination. The examples set forth are for purposes of illustration and are not to be construed as limitative of the present invention. Many variations of the process may be made without departing from the spirit and scope of the invention. In these examples, unless otherwise stated, all parts and percentages are by weight and all temperatures are in degrees Celsius. Product analyses shown were obtained by gas chromatography or nuclear magnetic resonance analysis.

EXAMPLE 1

A mixture of 63.3 parts of parachlorotoluene and 0.5 parts of bis(p-chlorophenyl) sulfide was charged to a reaction vessel. The mixture was heated to about 50° C and maintained at about that temperature while 25 parts of chlorine was introduced into the mixture, with agitation, over a period of about 3 hours. The reaction mixture was then purged with nitrogen to remove hydrogen chloride and any residual chlorine. Analysis of the reaction product showed 32 percent parachlorotoluene, 68 percent parachlorobenzyl chloride, and less than 1 percent nuclear chlorinated products.

EXAMPLE 2

The procedure of Example 1 was repeated except that: 0.5 parts of diphenyl sulfide was used in place of the bis(chlorophenyl)sulfide; and 46 parts of chlorine was introduced into the reaction mixture over a period of aout 10 hours. Analysis of the reaction product showed 17 percent parachlorotoluene, 71 percent parachlorobenzyl chloride, 12 percent parachlorobenzal chloride.

EXAMPLE 3

The procedure of Example 1 was repeated except that 0.5 parts of tetrachlorothiophene was employed in place of the bis(p-chlorophenyl) sulfide and 46 parts of chlorine was introduced into the reaction mixture over a period of about 11 hours. Analysis of the reaction product showed 11 percent parachlorotoluene, 82 percent parachlorobenzyl chloride and 7 percent parachlorobenzal chloride.

EXAMPLE 4

The procedure of Example 1 was repeated except that in place of the bis(p-chlorophenyl) sulfide, there was employed 0.5 parts of dioctylsulfide; and 35 parts of chlorine was introduced into the reaction mixture over a period of about 3.25 hours. Analysis of the reaction product established a composition of 16.5 percent parachlorotoluene, 70 percent parachlorobenzyl chloride and 13.5 parachlorobenzal chloride.

EXAMPLE 5

The procedure of Example 1 was repeated except that in place of the bis(p-chlorophenyl) sulfide, there was employed 2.53 parts of di-n-butyl-sulfide; and 142 parts of chlorine was introduced into the reaction mixture over a period of about 12 hours, while temperature of the reaction mixture was maintained at between about 50° and 60° C. Analysis of the reaction product established a composition of 12 percent parachlorotoluene, 72% parachlorobenzyl chloride, and 16 percent parachlorobenzal chloride.

EXAMPLE 6

A mixture of 63.3 parts of orthochlorotoluene and 0.5 parts of diphenyl sulfide was charged to a reaction vessel. The mixture was heated to about 50° C and maintained at about that temperature while 45 parts of chlorine was introduced into the mixture over a period of about 6 hours. The reaction product was then purged with nitrogen to remove hydrogen chloride and any residual chlorine. Analysis of the reaction product established a composition of 10 percent orthochlorotoluene, 88–90 percent orthochlorobenzyl chloride and 0–2 percent orthochlorobenzal chloride.

Table 1, below summarizes the results of the foregoing examples and compares the products thereof with products obtained when parachlorotoluene is chlorinated to approximately the same degree of conversion in a comparable photochemical reaction, using ultraviolet light in placeof the organic sulfide, to catalyze the reaction.

TABLE 1

Comparison of product composition* obtained from the organic sulfide catalyzed and photochemical catalyzed chlorination of parachlorotoluene (Examples 1–5) and orthochlorotoluene (Example 6).

| Ex. No. | Sulfide Catalyst | Percent Conversion** | Monochlorobenzyl chloride (percent) | | Monochlorobenzal chloride (percent) | |
|---|---|---|---|---|---|---|
| | | | Sulfide Catalyzed | Photochemical | Sulfide Catalyzed | Photochemical |
| 1 | Bis(p-chlorophenyl) Sulfide | 68 | 68 | 59 | 0 | 6 |
| 2 | Diphenyl Sulfide | 83 | 71 | 65 | 12 | 15 |
| 3 | Tetrachlorothiophene | 89 | 82 | 65 | 7 | 24 |
| 4 | Dioctylsulfide | 83.5 | 70 | 65 | 13.5 | 17.5 |
| 5 | Di-n-butylsulfide | 88 | 72 | 65 | 16 | 22 |

TABLE 1-continued

Comparison of product composition* obtained from the organic sulfide catalyzed and photochemical catalyzed chlorination of parachlorotoluene (Examples 1–5) and orthochlorotoluene (Example 6).

| Ex. No. | Sulfide Catalyst | Percent Conversion** | Monochlorobenzyl chloride (percent) | | Monochlorobenzal chloride (percent) | |
|---|---|---|---|---|---|---|
| | | | Sulfide Catalyzed | Photochemical | Sulfide Catalyzed | Photochemical |
| 6 | Diphenyl Sulfide | 90 | 88–90 | 69 | 0–2 | 25 |

*In all of the examples, less than 1.0 percent nuclear chlorinated products formed.
**Percent conversion indicates the total percent of chlorinated products.

What is claimed is:

1. A process for the mono-αchlorination of alkyl chloroaromatic compounds which comprises reacting chlorine with an alkyl chloroaromatic compound of the formula:

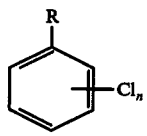

where R is methyl or ethyl and $n$ is 1 or 2; in the presence of a pre-prepared catalyst consisting essentially of an organic sulfide.

2. A process according to claim 1 wherein said catalyst is an organic sulfide selected from the group consisting of aryl sulfides, alkyl sulfides, alkyl aryl sulfides and heterocyclic sulfides, and is present in an amount of about 0.1 to about 10.0 weight percent by weight based on the weight of said alkyl chloroaromatic compound.

3. A process according to claim 1 which comprises reacting chlorine with monochlorotoluene in the presence of an organic sulfide catalyst selected from the group consisting of aryl sulfides, alkyl sulfides, alkyl aryl sulfides and heterocyclic sulfides.

4. A process according to claim 3 which comprises reacting chlorine with monochlorotoluene in the presence of about 0.1 to about 10.0 percent by weight of an aryl sulfide, based on the weight of monochlorotoluene.

5. A process according to claim 4 wherein said aryl sulfide is diphenyl sulfide.

6. A process according to claim 5 wherein chlorine is reacted with parachlorotoluene.

7. A process according to claim 5 wherein chlorine is reacted with orthochlorotoluene.

8. A process according to claim 4 which comprises reacting chlorine with parachlorotoluene in the presence of bis-(parachlorophenyl) sulfide.

9. A process according to claim 3 which comprises reacting chlorine with parachlorotoluene in the presence of about 0.1 to about 10.0 percent by weight of a heterocyclic sulfide, based on the weight of parachlorotoluene.

10. A process according to claim 9 wherein said heterocyclic sulfide is tetrachlorothiophene.

11. A process according to claim 3 which comprises reacting chlorine with parachlorotoluene in the presence of about 0.1 to about 10.0 percent by weight of an alkyl sulfide, based on the weight of parachlorotoluene.

12. A process according to claim 11 wherein said alkyl sulfide is dioctylsulfide.

13. A process according to claim 9 wherein said alkyl sulfide is di-n-butyl sulfide.

14. A process for the preparation of monochlorobenzyl chloride consisting essentially of reacting chlorine with monochlorotoluene at a temperature of about 20° to about 80° Celsius in the presence of 0.1 to about 10.0 percent by weight, based on the weight of monochlorotoluene, of a pre-prepared catalyst selected from the group consisting of diphenyl sulfide, bis(parachlorophenyl) sulfide, tetrachlorothiophene, dioctylsulfide, and di-n-butylsulfide.

15. A process according to claim 14 wherein said catalyst is present in an amount of about 0.5 to about 1.0 percent by weight, based on the weight of monochlorotoluene.

16. A process according to claim 15 wherein said monochlorotoluene is parachlorotoluene.

17. A process according to claim 15 wherein said monochlorotoluene is orthochlorotoluene.

18. A process according to claim 15 wherein said catalyst is diphenyl sulfide.

19. A process according to claim 15 wherein said catalyst is bis(parachlorophenyl) sulfide.

20. A process according to claim 15 wherein said catalyst is tetrachlorothiophene.

21. A process according to claim 15 wherein said catalyst is dioctylsulfide.

22. A process according to claim 15 wherein said catalyst is di-n-butyl-sulfide.

23. A process according to claim 17 wherein said catalyst is diphenyl sulfide.

* * * * *